(12) United States Patent
Fielder

(10) Patent No.: US 6,428,509 B1
(45) Date of Patent: Aug. 6, 2002

(54) SYRINGE PLUNGER DRIVER SYSTEM AND METHOD

(75) Inventor: Paul D. Fielder, Feltham (GB)

(73) Assignee: ALARIS Medical Systems, Inc., San Diego, CA (US)

( * ) Notice: Subject to any disclaimer, the term of this patent is extended or adjusted under 35 U.S.C. 154(b) by 0 days.

(21) Appl. No.: 09/362,970

(22) Filed: Jul. 29, 1999

(51) Int. Cl.$^7$ .............................................. A61M 37/00
(52) U.S. Cl. ........................ 604/154; 604/67; 604/131
(58) Field of Search ................................ 604/131, 134, 604/135, 151, 152, 154, 246, 65, 67, 155

(56) References Cited

U.S. PATENT DOCUMENTS

| | | | |
|---|---|---|---|
| 4,919,650 A | 4/1924 | Feingold et al. ............... 604/67 |
| 3,235,220 A | 2/1966 | Räntsch et al. .............. 248/346 |
| 3,259,077 A | 7/1966 | Wiley et al. ................. 103/227 |
| 3,447,479 A | 6/1969 | Rosenberg .................. 103/153 |
| 3,720,211 A | 3/1973 | Kyrias ......................... 128/218 |
| 3,842,690 A | 10/1974 | Gulick ........................... 74/625 |
| 3,858,581 A | 1/1975 | Kamen ........................ 128/218 |
| 3,886,938 A | 6/1975 | Szabo .......................... 128/218 |
| 3,994,294 A | 11/1976 | Knute .......................... 128/214 |
| 4,085,747 A | 4/1978 | Lee .............................. 128/214 |
| 4,155,490 A | 5/1979 | Glenn ........................ 222/327 |
| 4,191,087 A | 3/1980 | Wright ........................ 128/218 |
| 4,210,173 A | 7/1980 | Choksi et al. ............ 137/512.3 |
| 4,255,096 A | 3/1981 | Coker, Jr. et al. .......... 417/415 |
| 4,424,720 A | 1/1984 | Bucchianeri ................ 74/89.15 |
| 4,435,173 A | 3/1984 | Siposs et al. ................ 609/155 |
| 4,465,474 A | 8/1984 | Mardorf et al. ............. 605/154 |
| 4,529,401 A | 7/1985 | Leslie et al. ................. 604/131 |
| 4,544,369 A | 10/1985 | Skakoon et al. ............. 604/155 |
| 4,560,979 A | 12/1985 | Rosskopf ..................... 340/540 |
| 4,563,175 A | 1/1986 | LaFond ........................ 604/155 |
| 4,652,260 A | 3/1987 | Fenton, Jr. et al. ........... 604/67 |
| 4,767,406 A | 8/1988 | Wadham et al. ............ 604/155 |
| 4,804,368 A | 2/1989 | Skakoon et al. ............. 604/155 |
| 4,838,857 A | 6/1989 | Strowe et al. ................. 604/67 |
| 4,857,056 A | 8/1989 | Talonn ........................ 604/135 |
| 4,908,017 A | 3/1990 | Howson et al. ............... 604/67 |
| 4,931,041 A | 6/1990 | Faeser ......................... 604/155 |
| 4,952,205 A | 8/1990 | Mauerer et al. ............... 604/67 |
| 4,959,056 A | 9/1990 | Dombrowski et al. ...... 604/186 |
| 4,976,696 A | 12/1990 | Sanderson et al. .......... 604/154 |
| 4,988,337 A | 1/1991 | Ito .............................. 604/154 |
| 5,006,112 A | 4/1991 | Metzner ...................... 604/155 |
| 5,034,004 A | 7/1991 | Crankshaw ................. 604/154 |
| 5,236,416 A | 8/1993 | McDaniel et al. ............ 604/67 |
| 5,545,140 A * | 8/1996 | Conero et al. .............. 604/154 |
| 5,879,360 A * | 3/1999 | Crankshaw ................. 604/154 |

FOREIGN PATENT DOCUMENTS

| | | | |
|---|---|---|---|
| DE | 297 13 836 U1 | 9/1997 | ............ A61M/5/00 |
| EP | 0 323 321 A1 | 7/1989 | ............ A61M/5/14 |
| EP | 0 514 907 A1 | 11/1992 | .......... A61M/5/145 |
| EP | 0 916 353 A1 | 5/1999 | .......... A61M/5/145 |
| EP | 0916353 A1 * | 5/1999 | .......... A61M/5/145 |
| EP | 1 005 875 A2 | 6/2000 | .......... A61M/5/145 |
| EP | 1005875 A2 * | 6/2000 | .......... A61M/5/145 |
| FR | 2 628 636 A1 | 9/1989 | ............ A61M/5/20 |

* cited by examiner

Primary Examiner—Brian L. Casler
Assistant Examiner—Jennifer Maynard
(74) Attorney, Agent, or Firm—Fulwider Patton Lee & Utecht, LLP

(57) ABSTRACT

A syringe plunger driver system capable of engaging different sized syringes. A drive head includes a pushing surface as well as spaced-apart arms biased toward each other and toward the pushing surface. An activating lever moved to a first position moves the arms outward away from each other and forward toward the syringe barrel for ease in loading a syringe. Moving the lever to a second position permits the biasing devices connected to the arms to move the arms inward to capture the syringe plunger and then rearward to hold the plunger flange against the pushing surface to resist siphoning.

20 Claims, 13 Drawing Sheets

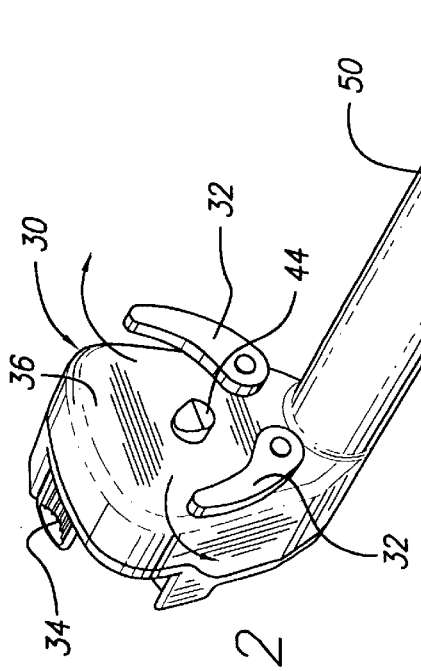
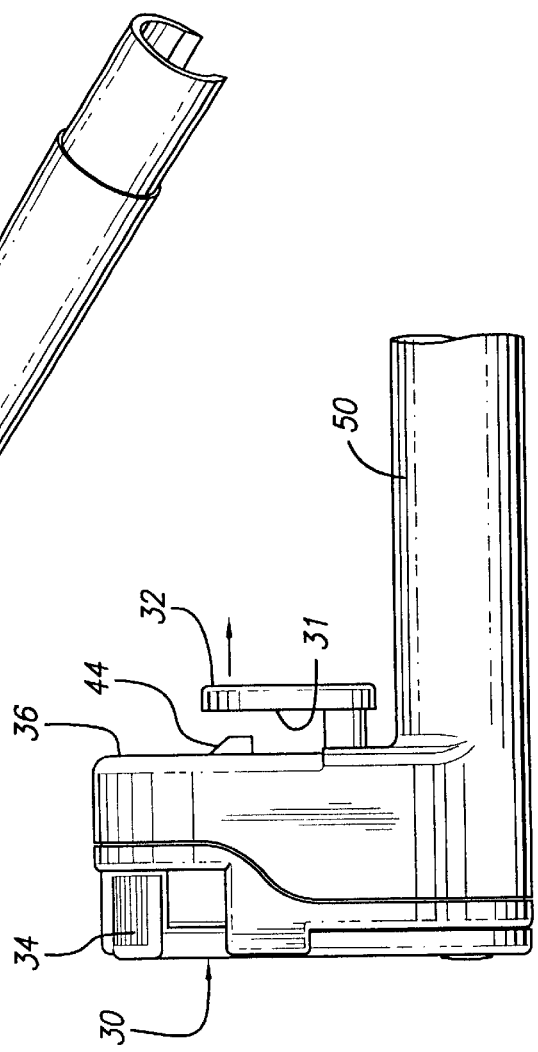
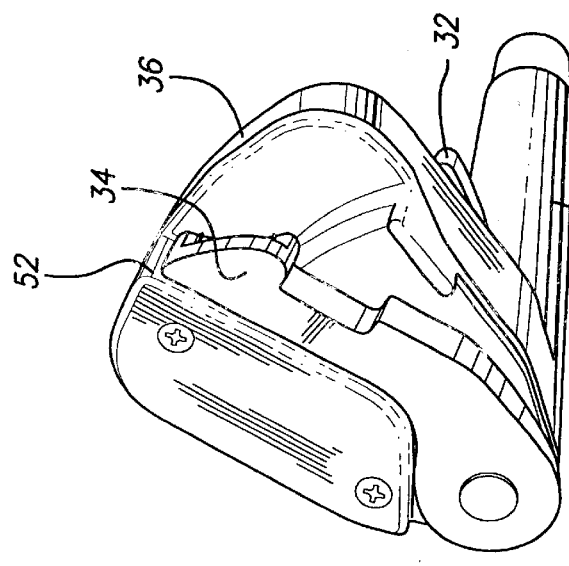

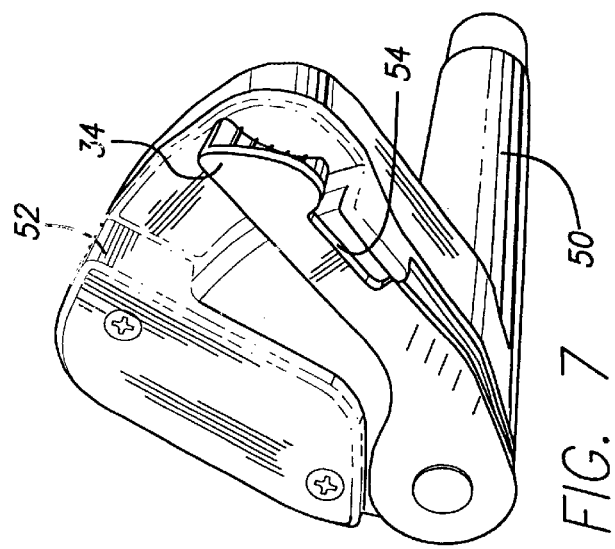
FIG. 7
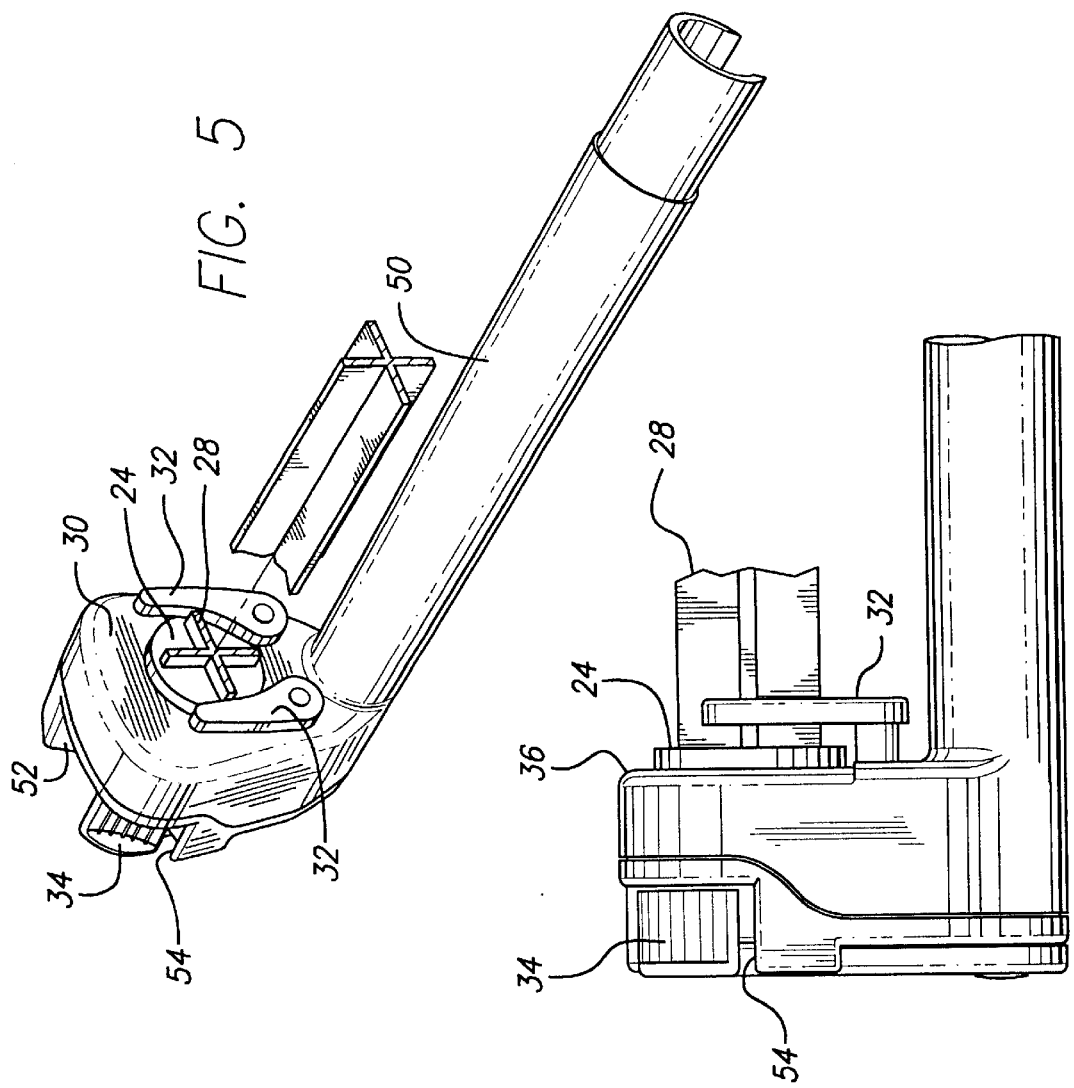
FIG. 5
FIG. 6

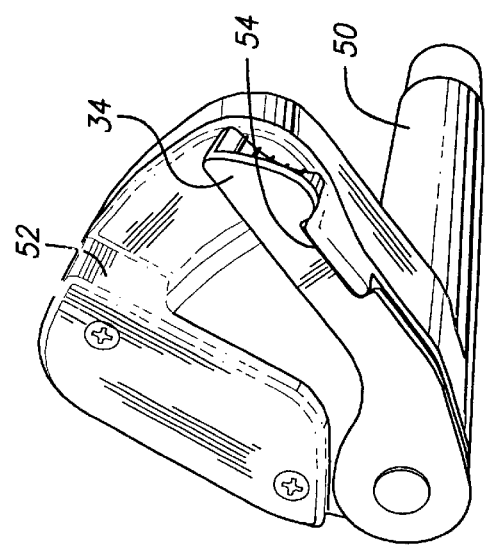
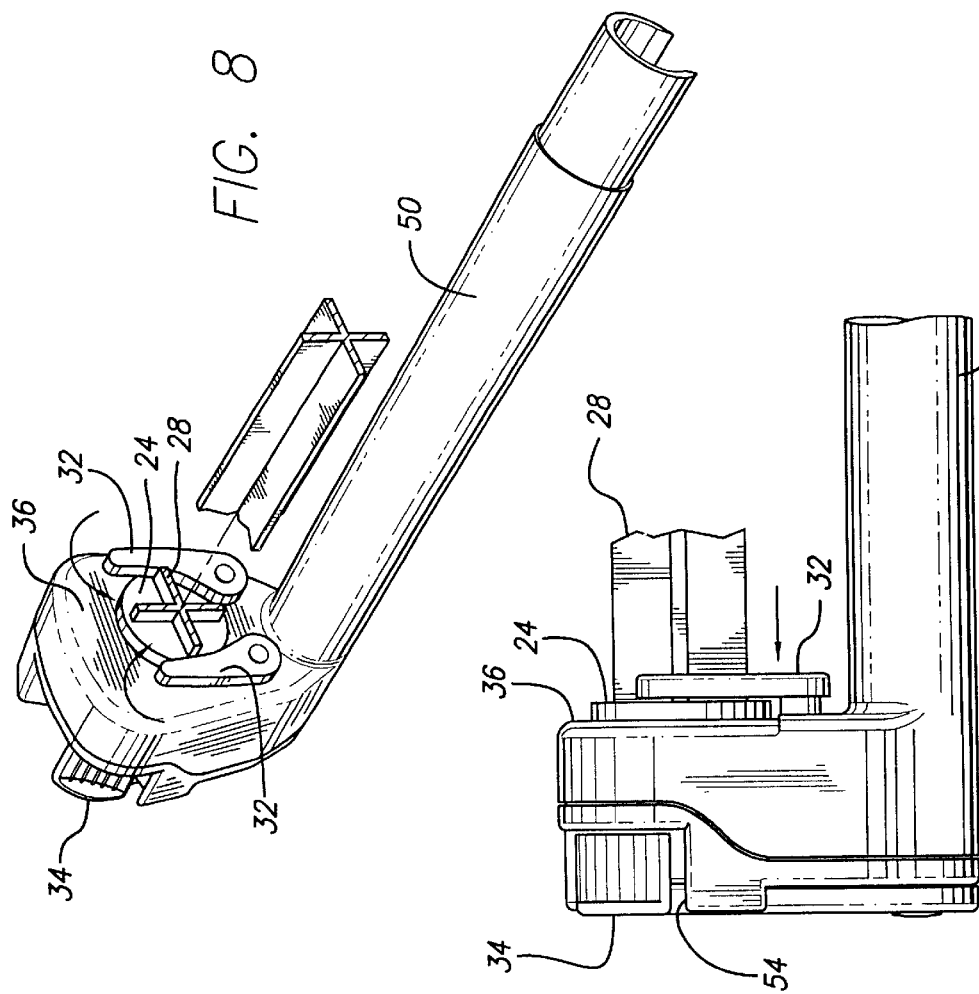

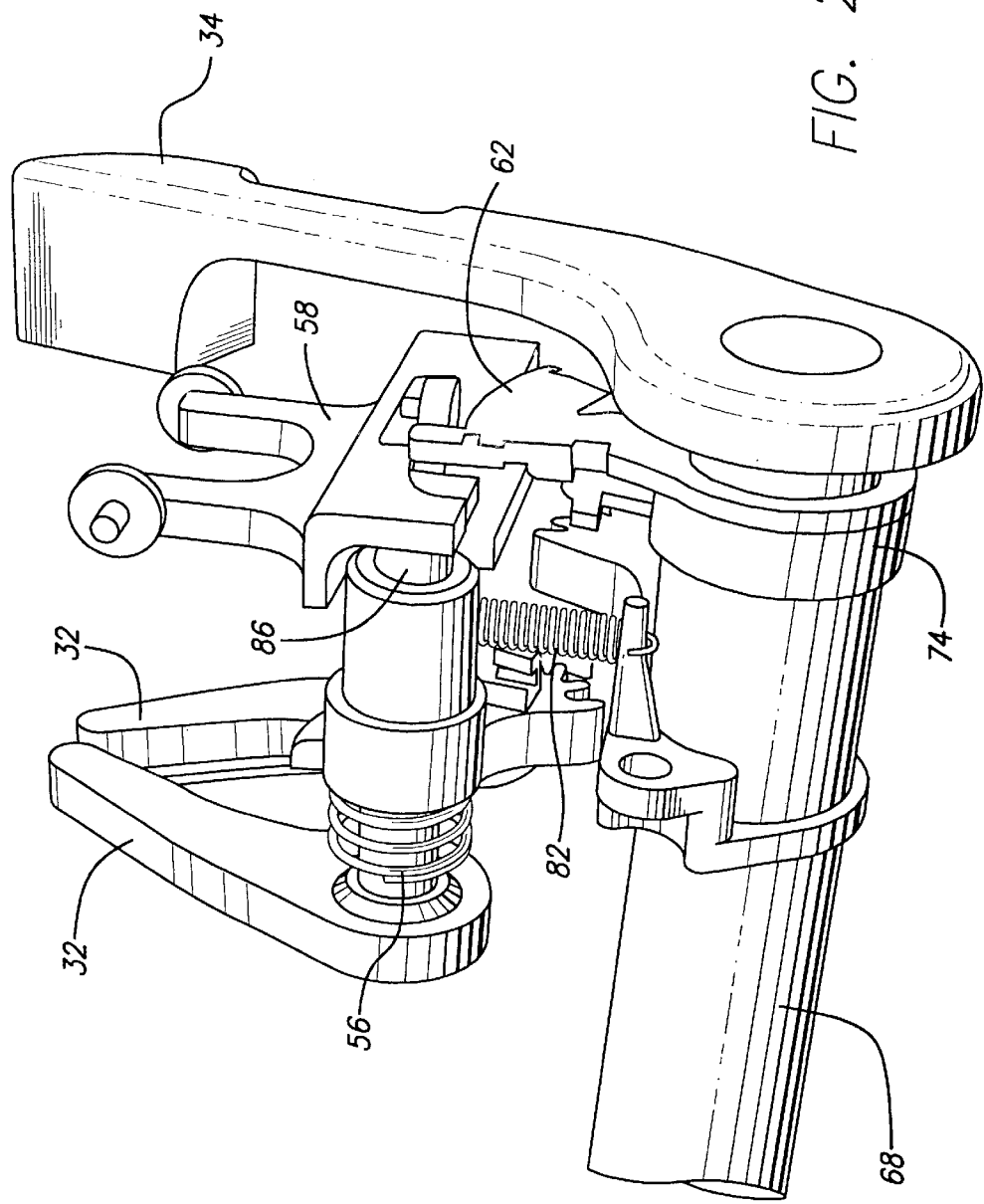

SYRINGE PLUNGER DRIVER SYSTEM AND METHOD

BACKGROUND

The invention is related generally to drive mechanisms for medical infusion pumps, and more particularly, to a system and method for retaining the plunger of a fluid container at the drive mechanism.

The infusion of fluids such as parenteral fluids into the human body is accomplished in many cases by means of a syringe pump having a lead screw and a screw drive mechanism which translates the rotational motion of the lead screw into linear motion. A syringe plunger driver is connected to the screw drive mechanism for connecting the linear motion of the screw drive mechanism to the syringe plunger to empty the syringe.

Because syringes are of different sizes and are filled to different levels with infusion fluids, the extension of the plunger from the syringe barrel will differ from syringe to syringe. Many screw drive mechanisms include a disengagement mechanism that the operator uses to disengage the lead screw drive mechanism from the lead screw threads. Once disengaged, the operator may move the plunger driver along the lead screw to the position of the extended syringe plunger, and then engage both the syringe plunger with the plunger driver and the lead screw drive mechanism with the threads of the lead screw at the new position. It is desirable that this disengagement mechanism and this plunger driver mechanism be easy to use to facilitate operator usage of the pump.

As is well known, syringes vary in size among manufacturers. Even syringes designed to contain the same quantity of fluid can vary substantially in outer dimensions of both length and diameter from manufacturer to manufacturer. In some prior pumps, only a single syringe from a single manufacturer could be used, thereby greatly restricting the usefulness of the pump. When that particular syringe type was not available, the pump could not be used. Pumps were also developed that could receive different sized syringes; however, obstacles still exist. Not only can syringe barrel diameters vary from syringe to syringe, but also the length of the syringe barrel, the plunger length, the plunger flange diameter, and thickness of the plunger flange can all vary. All of these physical variables would have to be considered when designing a plunger driver system for a syringe pump if that pump is to be capable of handling syringes of differing capacities from a variety of manufacturers.

In a syringe pump plunger driver, the driver typically engages the plunger flange and holds that flange in a fixed relationship with a pushing surface which is part of the plunger driver. The pushing surface contacts the plunger flange and applies force to move the plunger flange into the syringe to expel the syringe contents. Some plunger drivers include a retainer structure that operates as an anti-siphon feature to prevent the plunger from moving into the barrel and emptying the syringe at a rate in excess of the programmed movement rate of the pushing surface when under a negative pressure condition downstream. It is desirable to avoid a siphoning condition as the rate of administration of a fluid from the syringe is typically prescribed for a patient and exceeding that rate may not meet the requirements of the prescription. This is particularly true in the case where the medicament is to be administered to the patient at a very low flow rate. Even a small amount of siphoning can exceed the prescribed rate.

In the case where a syringe pump is to accommodate a wide variety of different syringe sizes, a plunger driver system is needed which will precisely hold each syringe in correct alignment with the pushing surface of the plunger driver. The system must also assure that the plunger will be firmly held in the plunger driver and that the plunger detector system will detect the presence and absence of a syringe and provide an alarm in the case of a dislodged or absent plunger. Additionally, it would be desirable if such a system were easy to use.

In the case of one syringe pump driver system, easy-to-use rotating arms exist that capture the plunger flange between themselves as well as capture the plunger flange at the driver. While this arrangement provided a substantial improvement in the art, the rotating arms are fixed in longitudinal position in relation to the driver and are located so that the driver system can accept a wide variety of syringes. Therefore, the longitudinal position of the rotating arms is selected to accommodate the thickest syringe plunger flange. Consequently, for thinner plunge flanges, some longitudinal movement between the driver and the arms can occur.

In another driver system, the syringe plunger flange is retained well but due to the configuration of the driver system, loading the syringe is often awkward. In one design known as the "sprung plate," a plate is mounted to the plunger drive head and is intended to trap the syringe plunger flange between itself and the pushing surface of the plunger drive. However, loading the syringe properly for this design is not intuitive. In most cases, operators attempt to load the syringe barrel first and then try to load the plunger. Difficulty is encountered when trying to load the plunger in this sequence as the plunger stem must now be forced outwards in order to locate the plunger flange behind the sprung plate. This in turn requires some movement of the syringe barrel; however, there is a barrel clamp over the syringe barrel which has a bias device trying to prevent this very movement.

Hence, those skilled in the art have recognized a need for a plunger driver system and method that are capable of handling different sizes of syringes while still presenting a relatively easy system to use to the operator of the pump. Such a system and method should provide a mechanism to align, firmly engage, and detect the presence of the plunger of each of the syringes specified for the pump. Further, such a system and method should be capable of resisting siphoning of the syringe contents from syringes of all sizes usable in the pump. The invention fulfills these needs and others.

SUMMARY OF THE INVENTION

The present invention is directed to a system and method for driving a syringe plunger while resisting siphoning. At the same time, the system and method in accordance with the invention permit the use of syringes of different sizes as well as facilitating the loading of a syringe.

In a first aspect in accordance with the invention, a syringe plunger driver system is provided for engaging syringe plungers of different sizes, each plunger having a plunger piston, a plunger flange, and a plunger stem interconnecting the piston with the flange and each plunger forming a part of a syringe, each syringe having a barrel into and out of which the plunger moves, each plunger flange having an inner side facing the syringe barrel and an outer side, the plunger driver system having a drive head adapted to move the syringe plunger into the syringe barrel in an operation mode, the driver system comprises a pushing surface located on the drive head adapted to press against the outer side of the plunger flange to move the flange toward the barrel during the operation mode, a plunger retainer located on the drive head adapted to engage the inner side of the plunger flange and retain the flange in contact with the pushing surface, the plunger retainer also adapted to adjust itself to the size of the plunger, and a first bias device connected with the plunger retainer to bias the plunger retainer towards the pushing surface, whereby siphoning is resisted.

In a further aspect, the driver system further comprises an activating lever interconnected with the plunger retainer and having a first position at which the lever moves the plunger retainer into a syringe plunger non-engagement position to permit easy loading of the syringe plunger in the driver system. In more detailed aspects, the activating lever in its first position moves the plunger retainer outward and forward into the syringe plunger non-engagement position in opposition to the first bias device. The first bias device comprises a spring connected with the plunger retainer that biases the retainer towards the pushing surface, the spring having enough force to retain a plunger flange positioned between the pushing surface and the retainer in contact with the pushing surface during the operation mode.

In other aspects in accordance with the invention, the plunger retainer comprises a first pivotally mounted arm and the first bias device is adapted to bias the first arm towards the pushing surface. The retainer further comprises a second bias device adapted to bias the first arm pivotally inward toward a plunger stem mounted in the syringe driver system. In more detailed aspects, the retainer further comprises a second pivotally mounted arm biased toward the pushing surface. A third biasing device is adapted to bias the second arm pivotally inward toward a plunger stem mounted in the syringe driver system. An activating lever is interconnected with the first and second arms and has a first position at which the lever pivotally moves the first and second arms outward and forward into a syringe plunger non-engagement position in opposition to the biasing force on the first and second arms whereby easy loading of a syringe plunger is facilitated. The lever is interconnected to the first and second arms such that when the lever is moved to its first position, the lever causes the arms to first move outward and then to move forward. Further, the arms are mounted to the drive head such that the arms adjust themselves to the size of the plunger mounted to the pushing surface. The lever has a second position at which the lever does not apply force opposing the biasing devices on the first and second arms so that the arms may move toward each other and toward the pushing surface to capture a syringe plunger. Further, the lever is interconnected to the first and second arms such that when the lever is moved to its second position, the lever causes the arms to first move inward toward each other and then to move toward the pushing surface.

Other aspects and advantages of the invention will become apparent from the following detailed description and the accompanying drawings, illustrating by way of example the features of the invention.

BRIEF DESCRIPTION OF THE DRAWINGS

FIG. 2 is a view of a plunger drive head as shown in FIG. 1 with the retaining arms shown in the open position;

FIG. 3 is rear view of FIG. 2 showing the position of the lever to achieve the configuration shown in FIG. 2;

FIG. 4 shows the longitudinal motion of the arms when the lever is moved to the position shown in FIG. 3;

FIG. 5 is a view of the retainer arms grasping a syringe plunger stem in response to internal biasing devices after the lever has been moved somewhat from the position shown in FIG. 3;

FIG. 6 is a side view of FIG. 5 showing the arms grasping the plunger stem but not yet fully engaged with the plunger flange;

FIG. 7 is a rear view of FIG. 5 showing the position of the lever;

FIG. 8 shows the retainer arms fully engages with a syringe plunger wherein the arms have captured the plunger stem and the flange;

FIG. 9 is a side view of FIG. 8 showing that the retainer arms have captured the plunger flange against the pushing surface so that siphoning is resisted;

FIG. 10 shows the lever fully in a second position where the retainer arms take the configuration shown in FIGS. 8 and 9;

FIG. 25 is an assembled view of a retainer mechanism usable in achieving the configurations of the arms shown in previous figures;

DETAILED DESCRIPTION OF PREFERRED EMBODIMENTS

Figure 1:
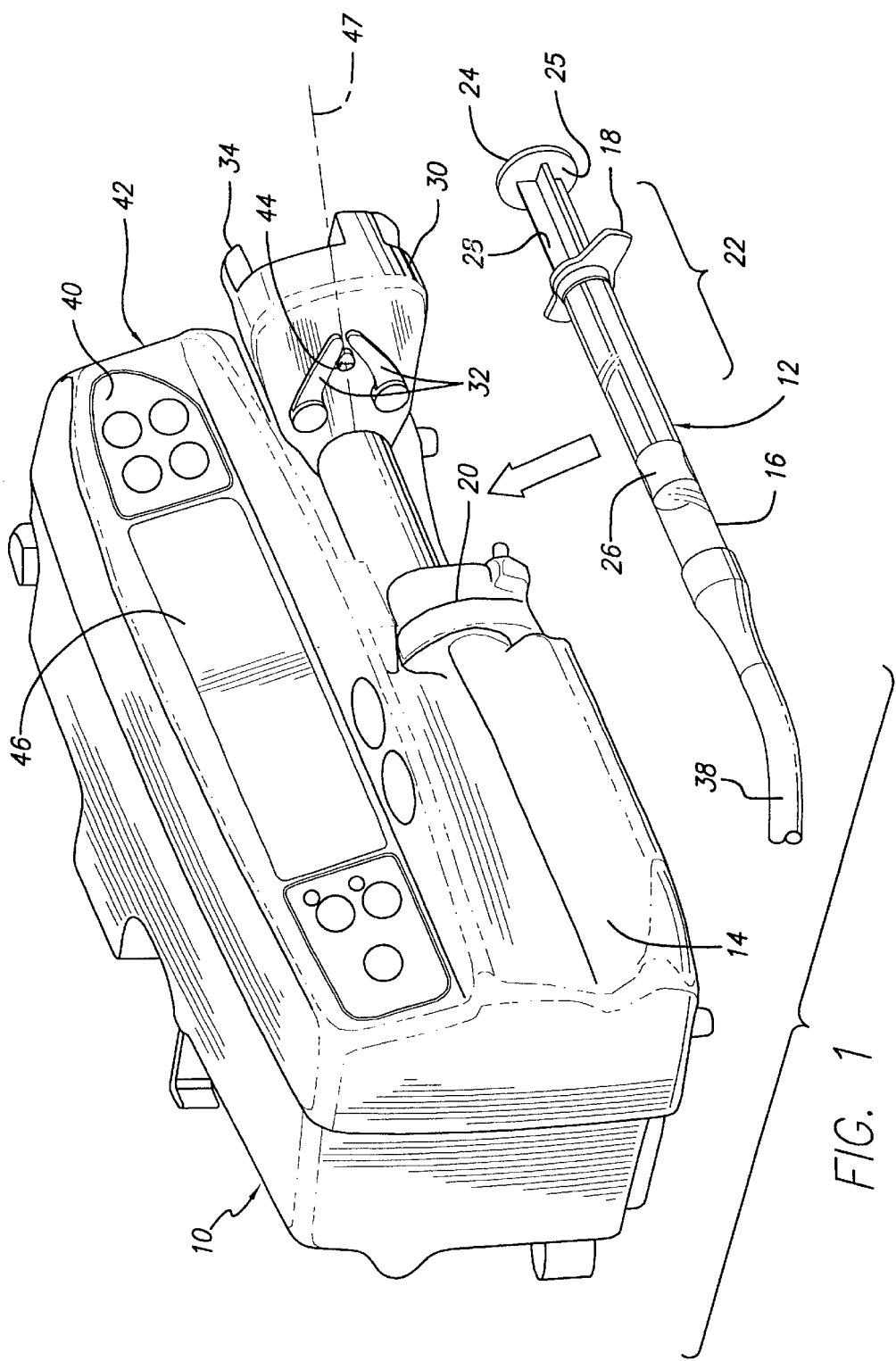
FIG. 1 is a perspective view of a syringe pump showing a plunger driver system in accordance with the principles of the invention and a typical syringe having a syringe barrel and syringe plunger.

Referring now to the drawings with more particularity, wherein like reference numerals designate like or corresponding elements among the several views, there is shown in FIG. 1 a perspective view of a syringe pump 10 having a plunger driver system in accordance with the principles of the invention. A syringe 12 is shown next to the pump rather than mounted in the pump, for clarity of illustration, with arrows indicating the mounting locations. The syringe pump includes a syringe cradle 14 in which the syringe barrel 16 will rest. The syringe barrel flange 18 will be located in a barrel flange groove 20 in the pump 10 to immobilize the syringe barrel from longitudinal movement during movement of the syringe plunger 22 within the barrel.

The syringe plunger flange 24, having an inner side 25, is interconnected with a syringe piston 26 by a syringe plunger stem 28. When mounted in the syringe pump 10 properly, the plunger flange 24 is held in a plunger drive head 30 with a pair of pivotally mounted plunger retaining arms 32, shown in the closed position in FIG. 1. A disengagement lever 34 is used to disengage the plunger drive head 30 from the threads of a lead screw (not shown) as well as control the positions of the retaining arms 32 to allow removal and insertion of a syringe plunger flange 24. Disengaging the plunger drive head 30 from the threads of the lead screw permits the operator to move the plunger drive head 30 along the lead screw to the correct position to capture the plunger flange of a new syringe 12. As is well known, syringes may be provided for use with a syringe pump with different quantities of fluid and the plunger may be located at different positions in relation to the barrel. The ability to manually move the drive head 30 permits the accommodation of syringes with different beginning plunger positions.

The drive head 30 also includes a pushing surface 36 on which the plunger flange 24 will rest as the drive head 30 moves forward toward the plunger barrel 16 pushing the plunger 22 into the barrel 16 of the syringe to expel the syringe contents through an administration tubing 38 to the patient. Also included in this embodiment of a plunger drive head is a detector button 44 used to detect the presence of a syringe. When the detector button 44 is depressed, circuitry within the drive head 30 indicates to a pump processor (not shown) that a syringe is present thereby enabling operation of the pump. In one embodiment, the pump will not operate if the detector button 44 has not been depressed, as may happen with a misloaded syringe, or a syringe that has become dislodged. Also included with the pump 10 is a control panel 42 comprising multiple buttons 40 for control over the pump 10 as well as a display 46 used to present pump specific information to the operator. The multiple button 40 may allow the operator to program the pump for the flow rate, the volume to be infused, and other pump parameters. The display may present the programmed flow rate, the amount of fluid remaining to be infused, as well as alarms and other information.

The cradle 14 of the pump 10 has a V-shape with an approximate 120° included angle. Syringes inserted in the cradle 14 will all align with the plunger driver 30 within a particular vertical range. The points where the longitudinal center lines of the syringes intersect the plunger driver will change according to the size of the syringe but only in one direction 47 along the drive head 30.

Referring now to FIG. 2, the plunger drive head 30 is shown in the open configuration where the retainer arms 32 have been moved outward (pivoted away from each other) and forward (longitudinally toward the syringe cradle 14 or the barrel 16 of a syringe if one is mounted in the pump). In this position or configuration, the drive head 30 is ready to accept a syringe plunger. Shown more clearly in FIG. 2 is the drive tube 50 that extends in one piece from the drive head 30 to a point within the body of the pump 10. This extended length serves to prevent spilled or leaking fluids from reaching the lead screw.

FIG. 3 presents a rear view of the drive head 30 shown in FIG. 2. In this view, the lever 34 has been moved to a first position causing the retainer arms 32 to be in the open position shown in FIG. 2. As is shown, the lever 34 has been moved fully into a first stop 52. In FIG. 4, a side view of both FIGS. 2 and 3, it can be seen that the arms 32 have also moved forward when they are in the open position. There is a space between the inside surfaces 31 of the arms 32 and the pushing surface 36 to accommodate a wide variety of plunger flange thicknesses. Also shown more clearly is the plunger detector button 44. In FIG. 4, the button 44 forming part of a plunger detector is shown in the extended position. Although not shown, a spring mounted internally to the drive head 30 is used to bias the detector button 44 outward. An optical sensor determines the presence and absence of a syringe plunger flange at the plunger drive head 30 by monitoring the position of the button 44. For further details concerning a syringe plunger detector system such as that shown and described here see U.S. Pat. No. 5,545,140 which is incorporated herein by this reference. In FIG. 4, the button 44 is completely forward indicating the absence of a plunger flange.

Another feature shown in FIG. 4 is the bevel formed into the top of the button 44. This bevel aids in syringe insertion into the pump 10 by allowing vertical motion during installation. The syringe plunger flange would strike the bevel causing the button 44 to depress somewhat while the syringe is being loaded. Without the beveled surface formed on the button 44, the syringe would have to be loaded more in a horizontal manner into the plunger drive head 30. With the bevel, the syringe may be loaded either horizontally or vertically thus making operator use of the pump easier.

Referring now to FIGS. 5, 6, and 7, the drive head 30 is shown in a partially closed configuration. The arms have pivoted inward, toward each other, to capture the plunger stem 28 between themselves to retain the syringe plunger in the correct radial position. To obtain this configuration, the lever 34 has been moved off the first stop 52 but has not been moved entirely over to a second stop 54. In this configuration, the arms have captured the plunger stem, but as shown in FIG. 6, they are not yet in contact with the plunger flange 24. There is still a space between the inside surfaces 31 of the arms 32 and the plunger flange as in FIG. 4. FIG. 7 shows the intermediate position of the lever more clearly. It should be noted that in this configuration, the lever is not midway between the first and second stops 52 and 54, but is closer to the second stop. In one embodiment, the lever does not cause the arms 32 to move toward the pushing surface until the last five degrees of movement of the lever 34. As is further discussed below, the arms 32 are self-adjusting to the size of plunger mounted in the pump. The arms 32 are spring loaded inward to provide a substantial clamping force against the stem of the plunger and as a result of that clamping force and the fact that sequencing of the arm movements is such that the arms close first before returning in the direction of the pushing surface, the plunger stem is first centered by the arms, and then is brought into contact with the pushing surface. Thus alignment of the plunger stem and flange is first obtained.

Turning now to FIGS. 8, 9, and 10, the closed configuration of the drive head 30 is shown. In this configuration, not only have the arms 32 captured the plunger stem 28 between themselves to retain the stem in the correct radial position (centered), but the inside surfaces 31 of the arms have also come into contact with the inside surface 25 of the plunger flange 24 to exert a clamping force against the flange towards the pushing surface (FIG. 9). The arms 32 provide a substantial clamping force against the inner side of the plunger flange to hold it constantly in contact with the pushing surface 36, thereby resisting siphoning. As is discussed below, spring loading of the arms is responsible for the force exerted by the arms against the plunger flange 24 to retain it in contact with the pushing surface. A large negative siphoning pressure greater than the spring force would be needed to overcome the force exerted by the arms 32 against the plunger flange 24. Unless such a negative force is provide, the arms will retain the plunger flange 24 in the correct position against the pushing surface so that the syringe contents are expelled in accordance only with the program of the pump. As is more clearly seen in FIG. 10, the lever 34 has been moved to the second stop 54 in this configuration.

Figure 11:
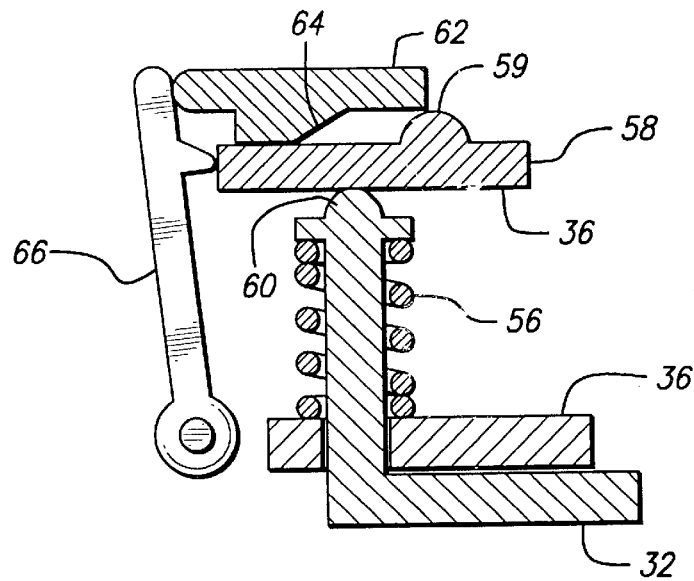
FIG. 11 is a mechanical schematic showing a system in accordance with principles of the invention where an actuation driver is at its rest position and the arm is at its closed position nominally in contact with the pushing surface.
Figure 12:
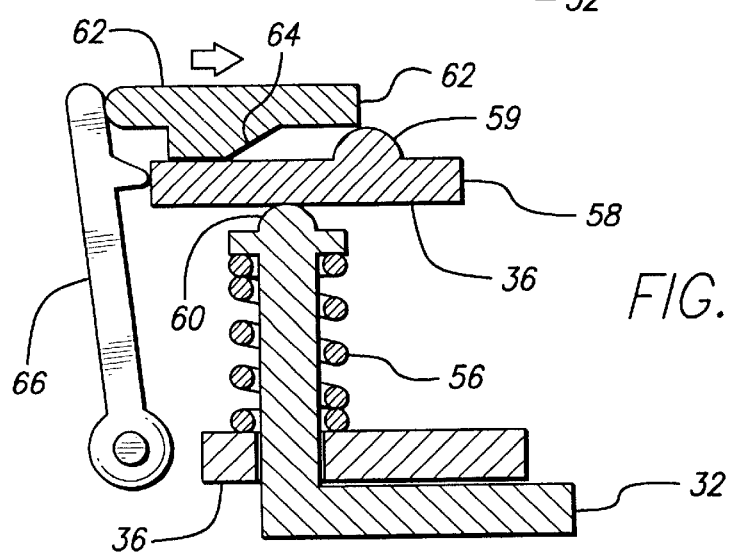
FIGS. 12 through 15 are schematics showing the sequence of action of the ramp of the actuation driver on the longitudinal position of the arm, as the control lever is moved to its open position.
Figure 13:
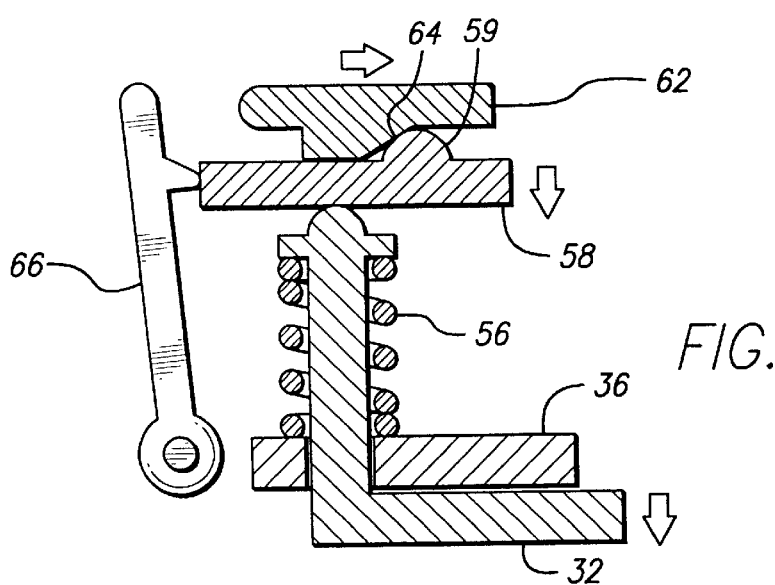
Figure 14:
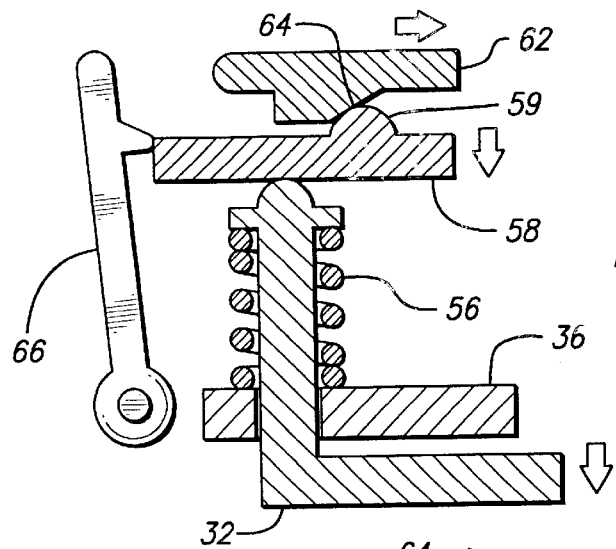

Turning now to schematic diagrams to show the operation of the retainer arms, FIGS. 11 through 18 present the operation of the arms in the longitudinal direction; i.e., toward the syringe barrel 16 and in the opposite direction, toward the pushing surface 36. In FIG. 11, an arm 32 is shown at its rest position. It is in contact with the pushing surface 36 or is a short distance away, that distance being less than the thickness of any known syringe flange that may be used in the pump. The arm 32 is biased into its rest position by a compression spring 56. An actuation plate 58 is in contact with the proximal end 60 of the arm and has a protrusion 59 on its surface away from the arm. The actuation plate moves towards and away from the pushing surface 36. An actuator driver 62 is in contact with the actuation plate 58 in FIG. 11 and moves laterally in relation to that plate 58, as is shown in FIGS. 12 through 18. The actuation driver 62 includes a ramp 64 for contacting the protrusion 59 of the actuation plate 58. A latch 66 is biased towards the actuation plate 58 and is shown touching the plate 58 in FIG. 11 but is not engaged with it. Although not shown, the lever 34 (FIG. 10) is coupled to the actuation driver 62 and the driver moves with the movement of the lever.

Figure 15:
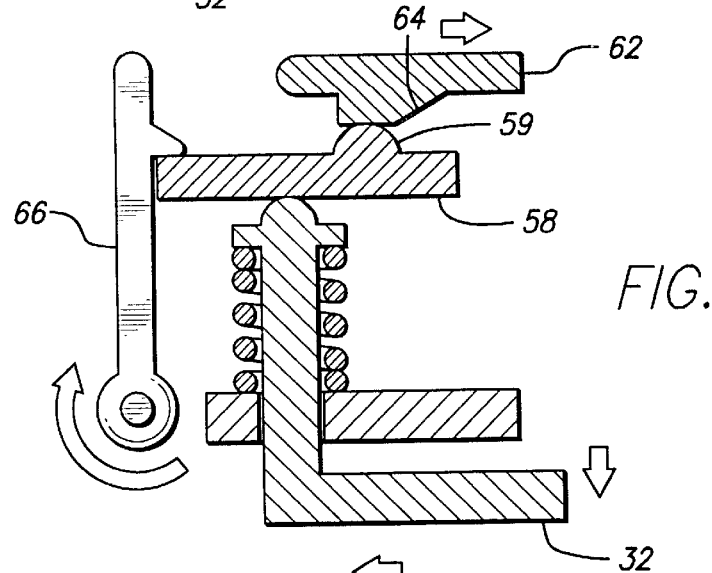

The following FIGS. 12 through 15 show the operation of the mechanism on the arm. As the lever and consequently the actuation driver 64 are moved toward the disengagement position (FIG. 3), the ramp 64 of the driver approaches the protrusion 59 of the actuation plate (FIG. 12), contacts the protrusion, and begins to extend the arm toward the syringe barrel, away from the pushing surface (FIGS. 13 and 14) thereby compressing the biasing spring 56. When the actuation driver 62 and arm have moved far enough so that the protrusion 59 of the actuation plate 58 is at the top of the ramp 64 as shown in FIG. 15, the latch engages the actuation plate.

Figure 16:
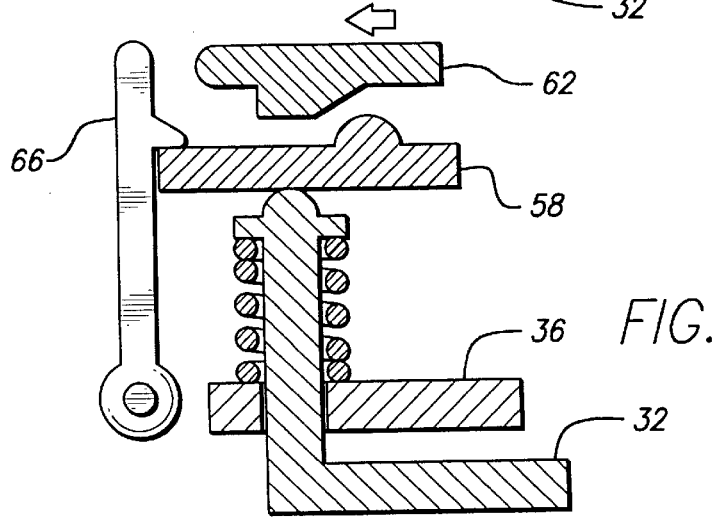
FIG. 16 shows the action of the latch on the actuating plate in holding it from further movement.
Figure 17:
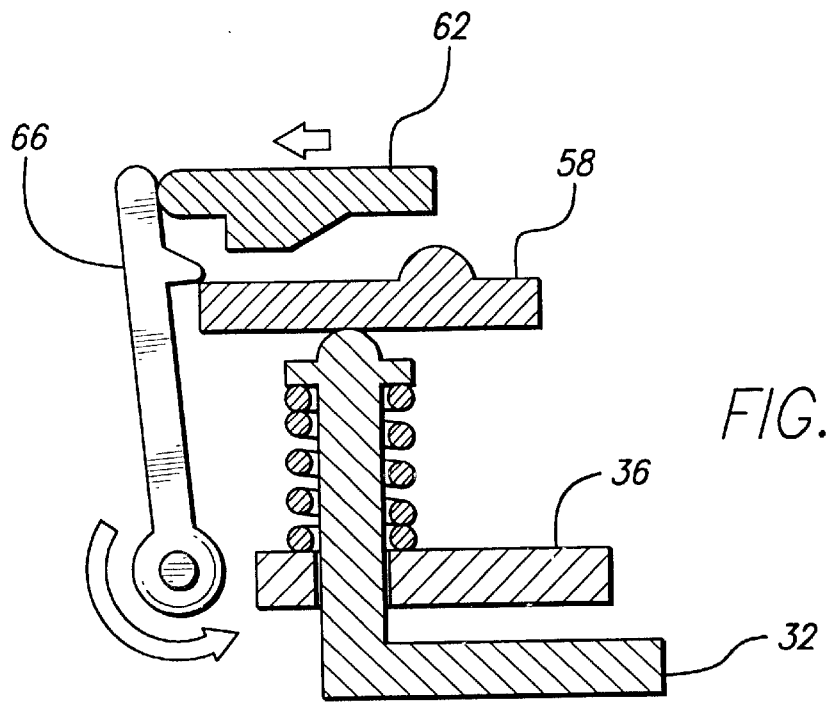
FIGS. 17 through 18 show the effect of the actuation driver in finally releasing the latch so that the arm may once again resume its rest position in nominal contact with the pushing surface.
Figure 18:
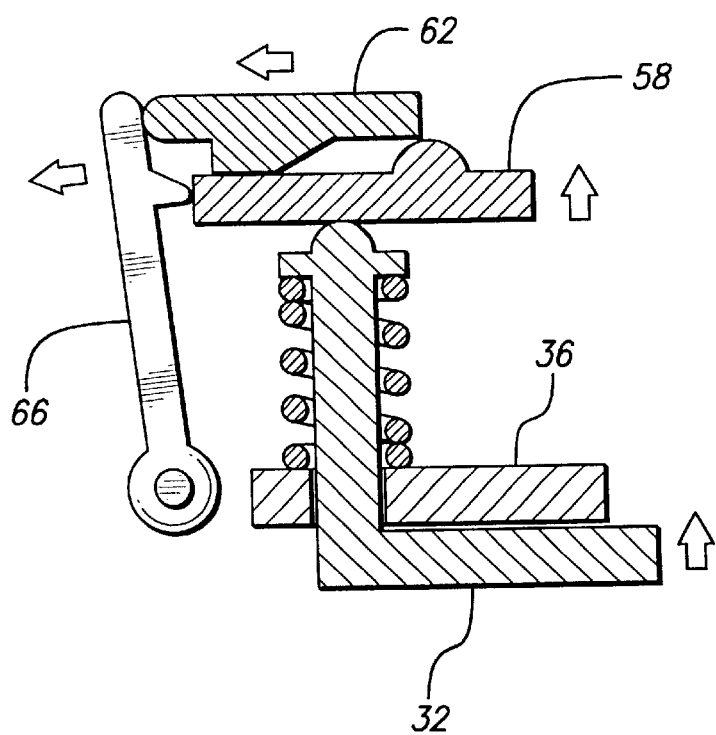
Figure 19:
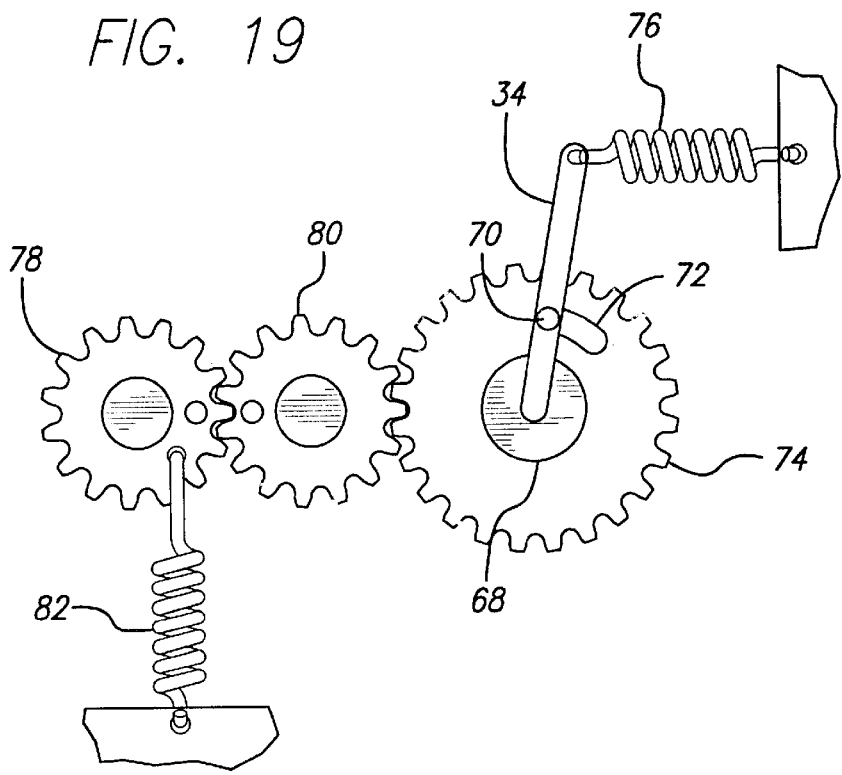
FIG. 19 shows the rest position of the lever gear controlled by the control lever, the lever gear being in contact with the arm gears of the two arms with the spring loading on the various components also shown.

As the lever and consequently the actuation driver 62 are moved toward the engagement position (FIG. 10), the ramp 64 of the actuation driver 62 loses contact with the protrusion 59 of the actuation plate 58 due to the engagement of the latch 66 with the actuation plate. Although the arms 32 remain in position during a large amount of movement of the actuation driver 62 as shown in FIGS. 16 and 17, the arms are rotating inward, as will be discussed below. When the actuation driver 62 has been moved far enough to the left, it contacts the latch (FIG. 17) and finally pushes the latch out of engagement with the actuation plate 58 in FIG. 18. The spring 56 of the arm then moves the arm 32 toward the pushing surface 36 and into contact with any syringe plunger flange that may be present. Additionally, the actuation plate 58 is once again in contact with the actuation driver 62. In the embodiment discussed above, the actuation driver 62 contacts the latch only in the last five degrees of movement of the lever. Thus the arms 32 are latched in the forward position until the last five degrees of movement of the lever 34.

The pivotal movement of the arms on the other hand occurs differently. Referring now to FIGS. 19 through 24, and in particular to FIG. 19 first, the lever 34 is connected to a mounting shaft 68, and has an actuation rod 70 captured within a slot 72 formed in an arms driver 74. An extension spring 76 biases the lever toward the right or closed position. Each of the arms (not shown) is connected to an arm drive gear 78 and 80. One of the drive gears 78 is biased by a bias extension spring 82 that tends to move the arm to the closed position (FIG. 1.

Figure 20:
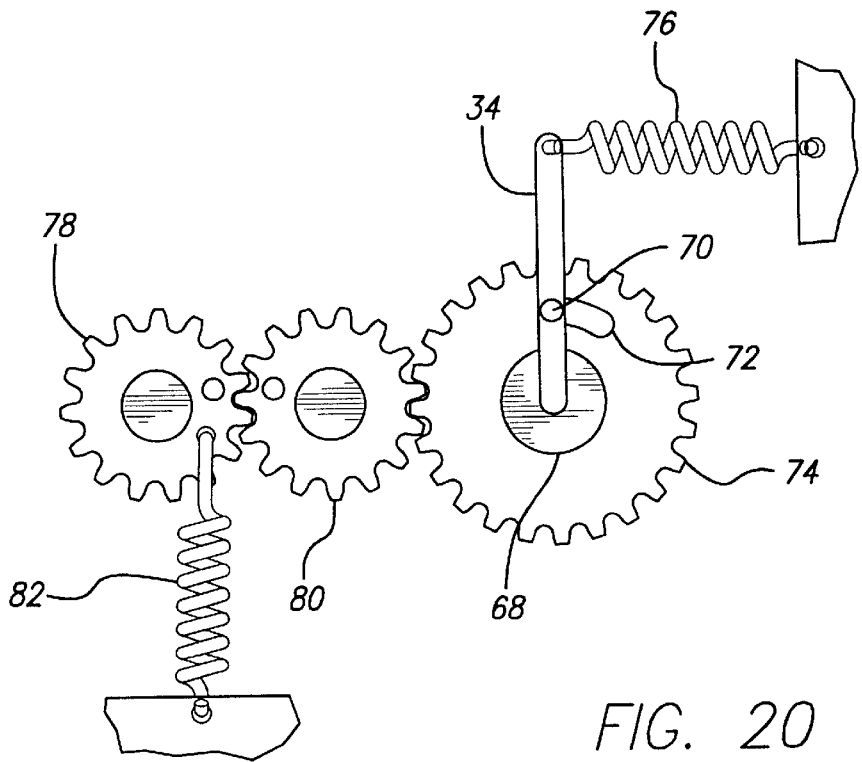
FIGS. 20 through 22 show the action of the gears as the control lever is moved to the open position.
Figure 21:
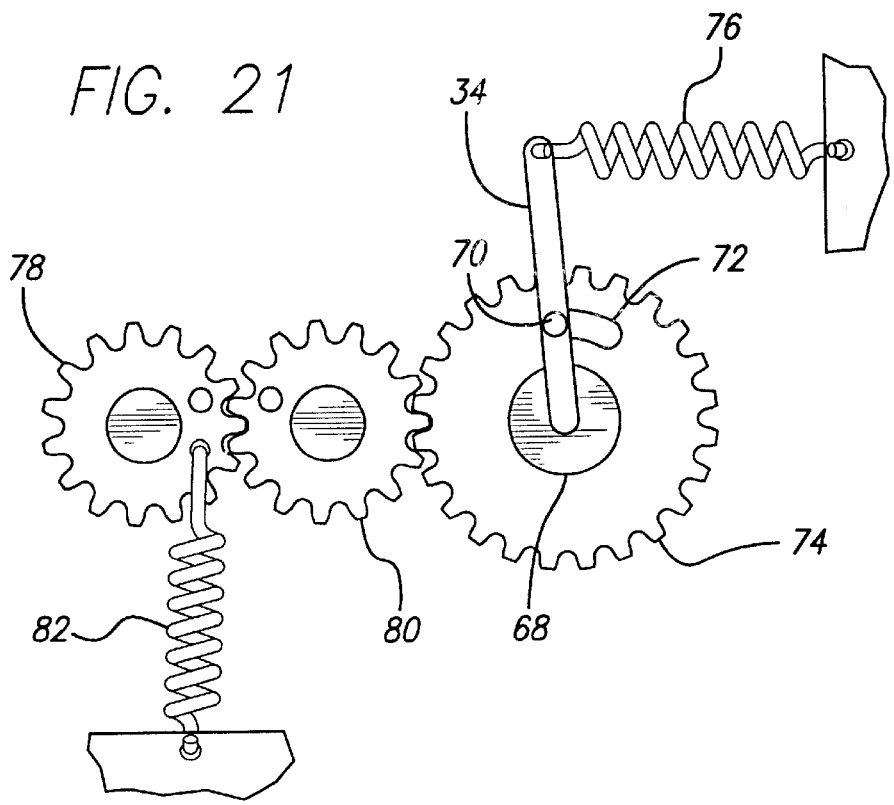
Figure 22:
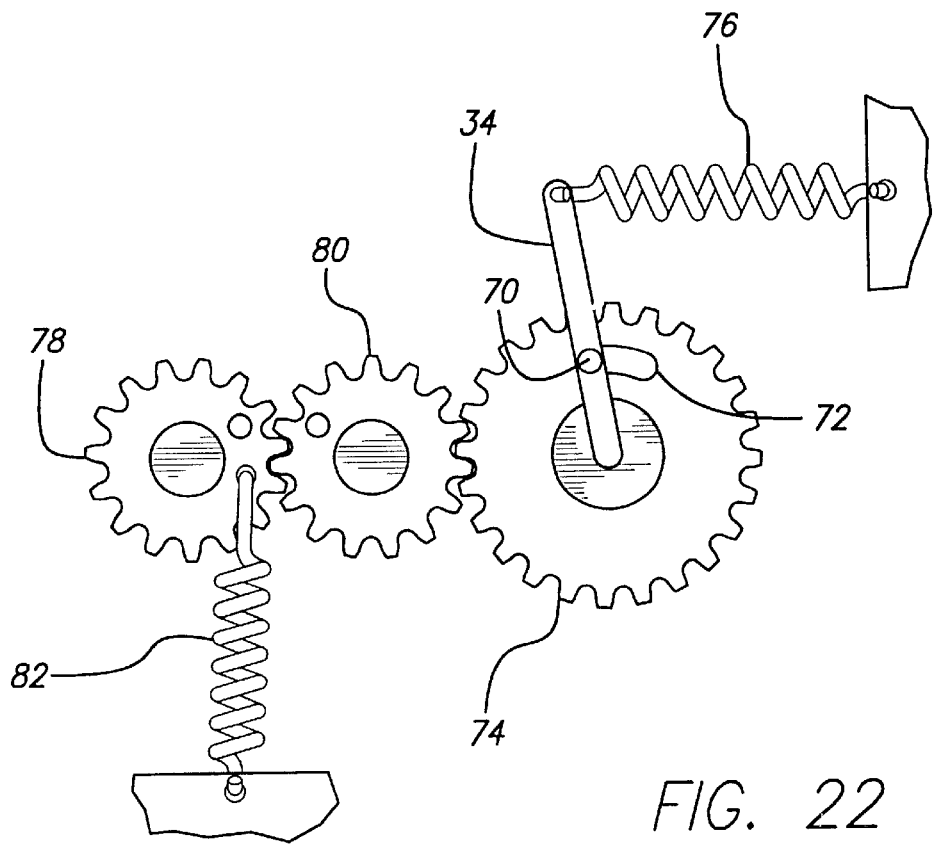

Referring now to FIGS. 20 through 24, the self-adjusting feature of the arms will be seen. As the lever is moved toward the disengaged position (FIG. 3), which is shown in FIGS. 20 through 22 as being moved counter-clockwise, the lever rod 70 engages an end of the slot 72 in the arms driver 74 causing the arms driver to rotate thus causing the arm drive gears 78 and 80 to rotate. This rotation causes the arms to move to the open position shown in FIG. 2. Opposing this motion are both the lever biasing spring 76 and the arm gear spring 82. At FIG. 22, the arms have reached the fully open position and the lever, rod, slot, and arms driver are holding the arms in that position against the forces provided by the springs 76 and 82.

Figure 23:
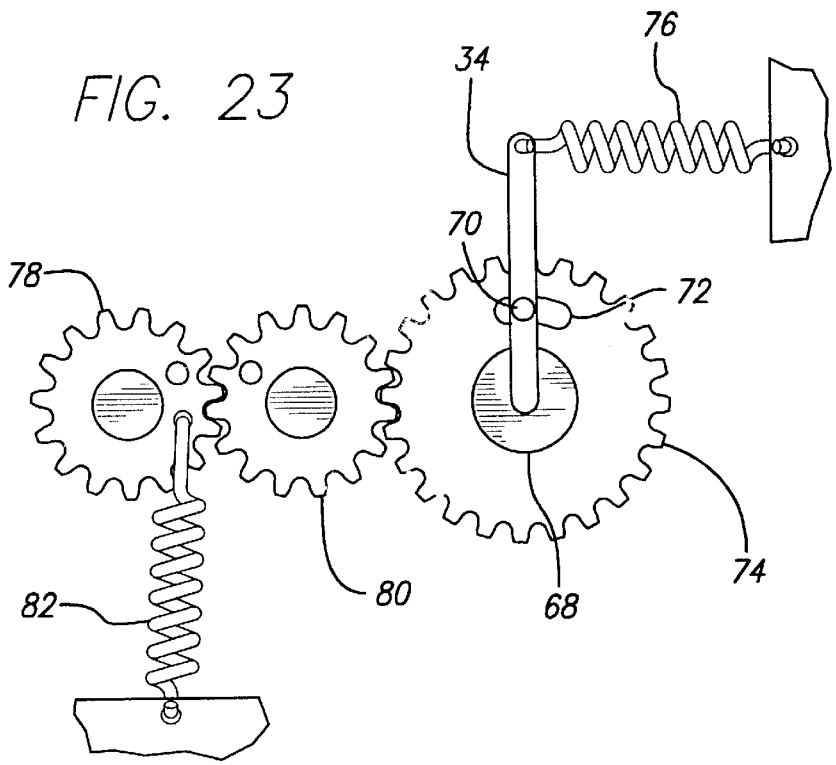
FIGS. 23 through 24 show the action of the gears as the control lever is moved to its closed position.
Figure 24:
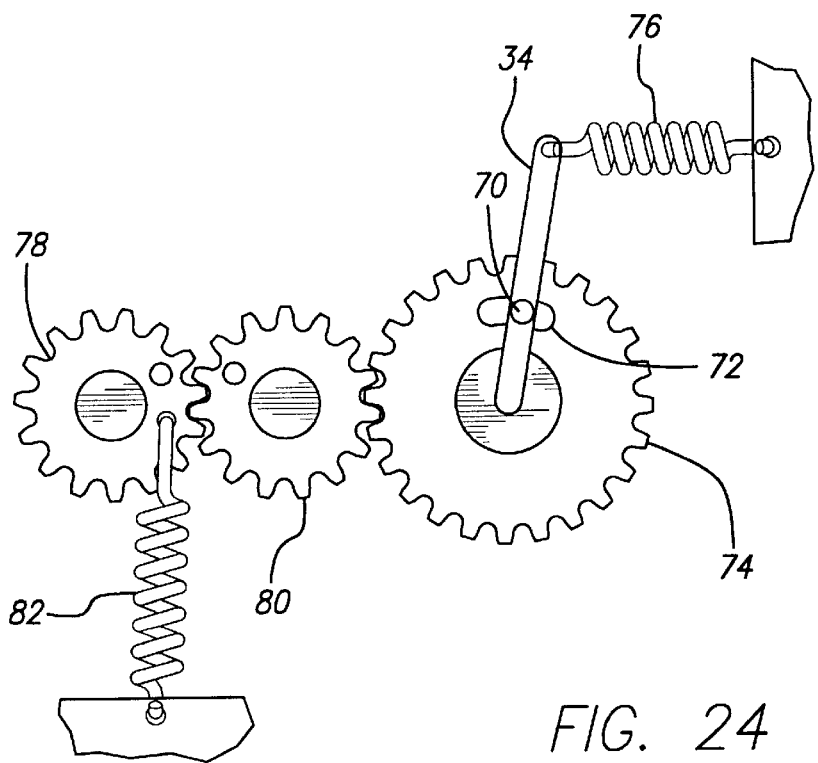

Referring now to FIGS. 23 and 24, the lever 34 is now being moved toward the closed position (FIG. 10) and the self-adjusting feature of the arms can be seen. Because the rod 70 of the lever 34 is in the slot 72 of the arms driver 74, movement of the lever in the clockwise direction does not cause movement of the arms driver 74. The slot 72 is made long enough to accommodate the entire range of pivotal movement of the arms. Thus when the lever is moved clockwise in the embodiment presented, it causes no movement of the arms driver 74 nor the arm gears 78 and 80, nor the arms. Instead, the arm gear biasing spring 82 will cause the arms to move toward the closed position (FIG. 1) or until the arms contact a plunger stem or a plunger flange depending on the thickness of the flange. Another feature of note is that the arms may pivot immediately inward as the lever is moved clockwise; they are not latched as they are in the longitudinal movement mechanism. Because the arms pivot inwards together simultaneously, they will tend to center the plunger stem or flange. FIG. 24 presents a view of the lever returned to the closed position shown in FIG. 10. One will notice therefore that in FIG. 19, the arms were closed much more than in FIG. 24 thus indicating that in FIG. 24, a syringe plunger has been installed between the arms.

Reference will now be made to a series of figures showing an embodiment where the schematics of FIGS. 11 through 24 have actually been incorporated into a single mechanism. Referring now to FIG. 25, the assembly of a lever/arms mechanism is shown without the drive head housing. The parts shown in FIG. 25 are also shown in FIGS. 26 through 29 as they are mounted in the housing, and are discussed in more detail below, after the discussion of FIG. 25. The lever 34 is pivotally connected to the drive gear 74 which is in turn connected to the mounting shaft 68. The lever is directly keyed to the mounting shaft 68. The drive gear 74 fits over the mounting shaft 68 and rotary motion of the lever 34 is decoupled with a fixed key on the shaft 68 and a side slot on the gear 74. This decoupling allows the mounting shaft 68 to drive the arms 32 open via the drive gear 74 and the arm gears 78 and 80 (which can be better seen in FIG. 26) during movement of the lever 34, and allows the arms 32 to close to a rest position once the lever is released. The load to close the arms is provided by the extension spring 82. The drive head 30 can therefore accommodate large diameter plungers and wide plunger ribs.

As discussed above, the arms 32 are sequenced such that they advance forward with rotation outwards generally simultaneously, but on return to the pushing surface 36, they remain extended forward until rotated closed and only then so they drop back to the pushing surface 36 (last five degrees of rotation of the lever in one embodiment). This enables the mounted syringe plunger to be first centered in relation to the driver head and then secured against the pushing surface. Syringe plungers of all diameter/thickness ratios may therefore be retained, and clamped against the pushing surface.

The lever 34 is also directly keyed to the activation driver 62. As the lever is rotated, a ball feature on the actuation plate 58 runs up the ramp feature on the activation driver 62. The actuation plate 58 then forces the arms 32 forward via ball bearings 86 and the arm gears 78 and 80, against a spring load. The ball bearings facilitate even loading on the gears from the actuation plate 58. When the arms are fully forward, the latch 66 (not shown) is allowed to rotate and locks the actuation plate 58 into its forward position. The actuation plate 58 remains locked forwards until the final return five degrees of travel of the lever 34, when the trigger feature on the activation driver 62 hits the latch 66 and the arms spring home under load from the compression springs 56. These compression springs 56 also provide the load that prevents the syringe from siphoning.

Figure 26:
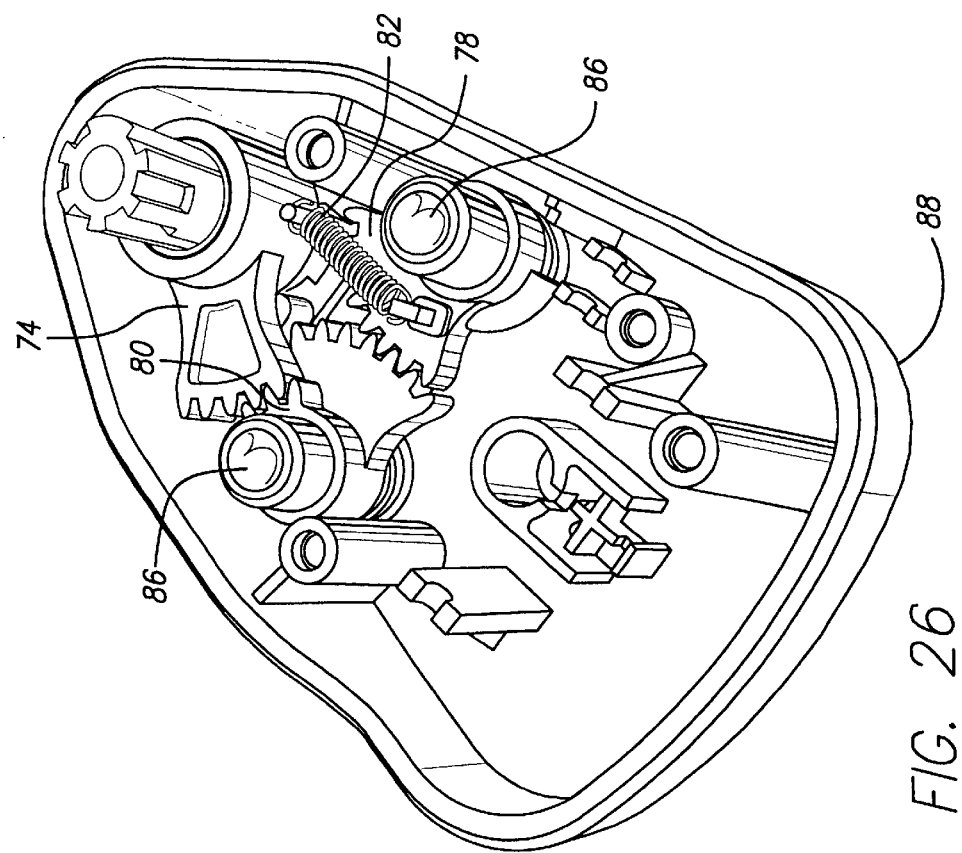
FIG. 26 shows an internal view of a drive head with part of the assembly shown in FIG. 25.

Turning now to FIGS. 26 through 29, the above features can be seen as they are mounted in the drive head housing 88. In FIG. 26, the arm pivoting mechanism can be more clearly seen. In particular, the arm gears 78 and 80, the extension spring biasing the arms (not shown) to the closed configuration, and the drive gear 74 meshing with the arm gears are shown. Also shown are the ball bearings mounted in each arm gear and the compression springs 56 that bias the arms to the rearward position against the pushing surface.

Figure 27:
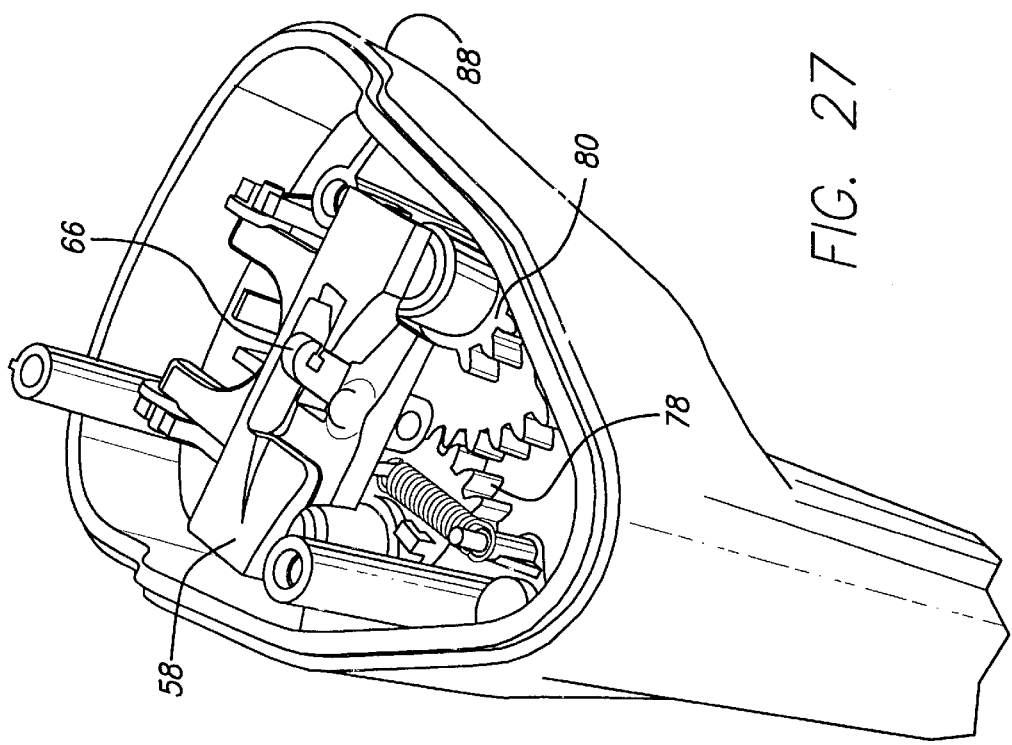
FIG. 27 shows an internal view of the drive head of FIG. 26 with additional parts of the assembly shown in FIG. 25.

In FIG. 27, the activating plate 58 has been added over the arm gears and as shown it is pivotally mounted so that it can apply pressure against the ball bearings of the arms. The drive gear 74 has been removed so that further detail can be seen.

Figure 29:
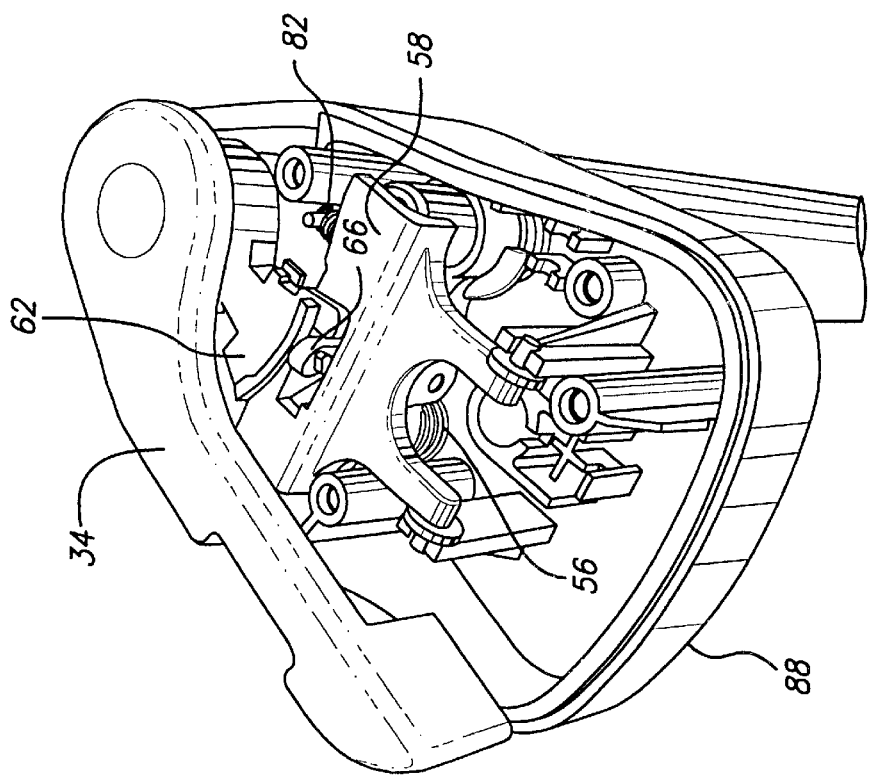
FIG. 29 shows an internal view of the drive head of FIG. 26 with additional parts of the assembly shown in FIG. 25.
Figure 28:
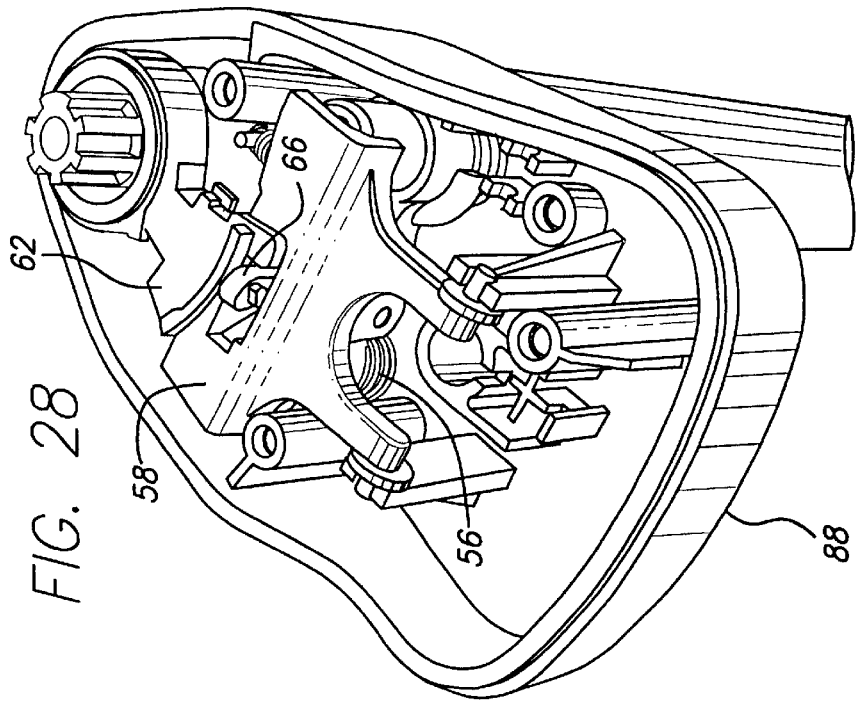
FIG. 28 shows an internal view of the drive head of FIG. 26 with additional parts of the assembly shown in FIG. 25.

FIG. 28 shows the installation of the latch 66 and FIG. 29 shows the components of FIG. 28 with the addition of the lever 34 mounted on the drive gear 74.

As a brief summary the arms 32 are individually pivoted in this embodiment and are spring biased to close toward each other. Each arm 32 is located through the front of the drive head housing 88 into respective inner arm gears 78 and 80. The extension spring 82 operates to bias the arms to the closed position (see FIG. 1).

Thus there are two independent biasing systems. Both operate on the retaining arms 32. The first operates to bias the retaining arms closed while the second biasing system operates to bias the arms toward the pushing surface. This independence of biasing systems allows for handling different syringes having different stem sizes as well as different plunger flange thicknesses.

Although there are two independent biasing systems, there is a single activating lever 34. The connecting system between the lever 34 and the arms 32 permits the two separate and sequenced motions of the arms as described above.

From the foregoing, it will be appreciated that the plunger driver system in accordance with the principles of the invention provides a versatile system to accept various sizes of syringes and results in easier pump operation as well as resists any siphoning whatsoever.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

What is claimed is:

1. A syringe plunger driver system for engaging syringe plungers of different sizes, each plunger having a plunger piston, a plunger flange, and a plunger stem interconnecting the piston with the flange and each plunger forming a part of a syringe, each syringe having a barrel into and out of which the plunger moves, each plunger flange having an inner side facing the syringe barrel and an outer side, the plunger stems and plunger flanges also varying in size, the plunger driver system having a drive head adapted to move the syringe plunger into the syringe barrel in an operation mode, the driver system comprising:

a pushing surface located on the drive head adapted to press against the outer side of the plunger flange to move the flange toward the barrel during the operation mode;

a plunger retainer located on the drive head adapted to permit the location of the syringe plunger flange in proximity to the pushing surface and to move to grasp the plunger stem and to engage the inner side of the plunger flange and retain the flange in contact with the pushing surface, the plunger retainer comprising a first arm and a second arm that move outward and forward in relation to the pushing surface to accept the plunger stem and flange between them, and that move toward each other so that both arms contact and capture the plunger stem between them, the distance that the arms move inward toward each other being self-adjusting to capture stems of different sizes; and a first bias device connected with the plunger retainer to bias the plunger retainer towards the pushing surface, whereby siphoning is resisted.

2. The driver system of claim 1 further comprising an externally mounted activating lever that an operator may touch and manipulate and that is interconnected with the plunger retainer and having a first position at which the lever moves the plunger retainer into a syringe plunger non-engagement position to permit easy loading of the syringe plunger in the driver system.

3. The driver system of claim 2 wherein the activating lever in its first position moves the plunger retainer outward and forward into the syringe plunger non-engagement position in opposition to the first bias device.

4. The driver system of claim 1 wherein the first bias device comprises a spring connected with the plunger retainer that biases the retainer towards the pushing surface, the spring having enough force to retain the plunger flange positioned between the pushing surface and the retainer in contact with the pushing surface during the operation mode.

5. The driver system of claim 1 wherein the first bias device is adapted to bias the first arm towards the pushing surface.

6. The driver system of claim 5 further comprising a second bias device adapted to bias the first arm pivotally inward toward the plunger. stem mounted in the syringe driver system.

7. The driver system of claim 5 wherein the second arm is pivotally mounted and is biased toward the pushing surface.

8. The driver system of claim 7 further comprising a third biasing device adapted to bias the second arm pivotally inward toward the plunger stem mounted in the syringe driver system.

9. The driver system of claim 7 further comprising an externally mounted activating lever that an operator may touch and manipulate and that is interconnected with the first and second arms and having a first position at which the lever pivotally moves the first and second arms outward and forward into a syringe plunger non-engagement position in opposition to a biasing force on the first and second arms whereby easy loading of a syringe plunger is facilitated.

10. The driver system of claim 9 wherein the lever is interconnected to the first and second arms such that when the lever is moved to its first position, the lever causes the arms to first move outward and then to move forward.

11. The driver system of claim 10 wherein the arms are mounted to the drive head such that the arms adjust themselves to the size of the plunger mounted to the pushing surface.

12. The driver system of claim 9 wherein the lever has a second position at which the lever does not apply force opposing the biasing devices on the first and second arms so that the arms may move toward each other and toward the pushing surface to capture the syringe plunger.

13. The driver system of claim 12 wherein the lever is interconnected to the first and second arms such that when the lever is moved to its second position, the lever causes the arms to first move inward toward each other and then to move toward the pushing surface.

14. The driver system of claim 1 wherein the plunger retainer comprises:
   a second biasing device connected to the arms to bias the arms toward each other to engage the syringe plunger.

15. The driver system of claim 14 further comprising an externally mounted activating lever that an operator may touch and manipulate and that is interconnected with the first and second arms and having a first position at which the lever pivotally moves the first and second arms outward and forward into a syringe plunger non-engagement position in opposition to biasing forces on the arms, and a second position at which the lever does not apply force opposing biasing forces applied to the first and second arms so that the arms may move toward each other and toward the pushing surface to capture the syringe plunger whereby siphoning is resisted.

16. A plunger driver system for engaging syringe plungers of different sizes, each plunger having a plunger piston, a plunger flange, and a plunger stem interconnecting the piston with the flange, wherein each plunger forms a part of a syringe, each syringe having a barrel into and out of which the plunger moves, each plunger flange having an inner side facing the syringe barrel and an outer side, the plunger stems and plunger flanges also varying in size, the plunger driver system having a drive head adapted to move the syringe plunger into the syringe barrel in an operation mode, the driver system comprising:
   a pushing surface located on the drive head adapted to press against the outer side of the plunger flange to move the flange toward the barrel during the operation mode;
   a first pivotally mounted arm mounted to the drive head, the first arm adapted to move outward and forward away from the pushing surface;
   a second pivotally mounted arm mounted to the drive head at a location spaced-apart from the first arm, the second arm adapted to move outward away from the first arm and forward away from the pushing surface;
   a first bias device adapted to bias the first and second arms towards the pushing surface;
   a second bias device adapted to bias the first and second arms inward toward each other; and
   an activating lever interconnected with the first and second arms and having a first position at which the lever pivotally moves the first and second arms outward from each other and forward away from the pushing surface into a syringe plunger non-engagement position in opposition to a biasing force on the arms for loading of the syringe plunger, and a second position at which the lever does not apply force opposing biasing forces applied to the first and second arms so that the arms may move toward each other and toward the pushing surface to capture the syringe plunger and maintain the plunger at the pushing surface whereby siphoning is resisted;
   wherein the first and second arms move toward each other so that both arms contact and capture the plunger stem between them, the distance that the arms move inward toward each other being self-adjusting to capture stems of different sizes.

17. The driver system of claim 16 wherein the arms are mounted to the drive head such that the arms adjust themselves to the size of the plunger mounted to the pushing surface.

18. A method for engaging syringe plungers of different sizes, each plunger having a plunger piston, a plunger flange, and a plunger stem interconnecting the piston with the flange, wherein each plunger forms a part of a syringe, each syringe having a barrel into and out of which the plunger moves, each plunger flange having an inner side facing the syringe barrel and an outer side, the plunger stems and plunger flanges also varying in size, the plunger driver system having a drive head adapted to move the syringe plunger into the syringe barrel in an operation mode, the method comprising the steps of:
   opening first and second pivotally mounted arms mounted to the drive head in a spaced-apart configuration outward away from each other;
   moving the first and second arms forward toward the syringe barrel to permit loading of the syringe plunger;
   after the syringe plunger has been positioned at the drive head, moving the first and second arms toward each other so that both arms contact and capture the plunger stem between them, the distance that the arms move inward toward each other being self-adjusting to capture stems of different sizes; and
   moving the first and second arms rearward toward the pushing surface to capture the syringe flange against the pushing surface whereby siphoning is resisted.

19. The method of claim 18 further comprising the step of moving an externally mounted activating lever that an operator may touch and manipulate and that is interconnected with the first and second arms to a first position at which the lever pivotally moves the first and second arms outward and forward into a syringe plunger non-engagement position whereby easy loading of the syringe plunger is facilitated.

20. The method of claim 19 further comprising the steps of:
   applying biasing forces to the first and second arms to bias them inward toward each other and biasing them toward the pushing surface; and
   moving the lever to a second position at which the lever does not apply force opposing the biasing devices on the first and second arms so that the arms may move toward each other and toward the pushing surface to capture the syringe plunger and maintain the plunger flange against the pushing surface whereby siphoning is resisted.

* * * * *

UNITED STATES PATENT AND TRADEMARK OFFICE
CERTIFICATE OF CORRECTION

PATENT NO.     : 6,428,509 B1
DATED          : August 6, 2002
INVENTOR(S)    : Paul D. Fielder It is certified that error appears in the above-identified patent and that said Letters Patent is hereby corrected as shown below:

Title page,
Item [56], References Cited, FOREIGN PATENT DOCUMENTS, delete duplication "1005875   A2   6/2000   A61M/5/145".

Column 5,
Line 43, "button 40", should read -- buttons 40 --.

Column 8,
Line 10, "(FIG. 1.", should read -- (FIG. 1). --.

Signed and Sealed this

Fifteenth Day of October, 2002

*Attest:*

JAMES E. ROGAN
*Attesting Officer*          *Director of the United States Patent and Trademark Office*